United States Patent
Kato et al.

(10) Patent No.: US 10,219,532 B2
(45) Date of Patent: Mar. 5, 2019

(54) STERILIZATION TRAY AND MOIST HEAT STERILIZATION METHOD

(71) Applicant: FUJIFILM Corporation, Tokyo (JP)

(72) Inventors: Nobuhiko Kato, Ashigarakami-gun (JP); Takashi Urabe, Ashigarakami-gun (JP); Michiko Kano, Toyama (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 388 days.

(21) Appl. No.: 15/144,883

(22) Filed: May 3, 2016

(65) Prior Publication Data
US 2016/0242453 A1    Aug. 25, 2016

(30) Foreign Application Priority Data

Nov. 5, 2013   (JP) .................................. 2013-229349

(51) Int. Cl.
*A61L 2/07*   (2006.01)
*A23L 3/10*   (2006.01)
(Continued)

(52) U.S. Cl.
CPC .............. *A23L 3/10* (2013.01); *A23L 3/001* (2013.01); *A61L 2/07* (2013.01); *A23V 2002/00* (2013.01); *A61J 1/10* (2013.01); *A61L 2202/23* (2013.01)

(58) Field of Classification Search
CPC ....................................................... A61L 2/07
See application file for complete search history.

(56) References Cited

U.S. PATENT DOCUMENTS 3,929,569 A * 12/1975 Piepers .................... F16F 1/18
376/441
4,632,026 A   12/1986 Yamamoto et al.
(Continued)

FOREIGN PATENT DOCUMENTS

EP   1 862 082 A2   12/2007
JP   48048665 A      7/1973
(Continued)

OTHER PUBLICATIONS

English Translation of Taguchi JP 58161814 dated Oct. 1983 (Year: 1983).*
(Continued)

*Primary Examiner* — Donald R Spamer
(74) *Attorney, Agent, or Firm* — Sughrue Mion, PLLC

(57) ABSTRACT

A sterilization tray is composed of a tray body and a pressing member capable of moving in a direction perpendicular to the tray body. The bottom of the tray body is formed from a perforated plate through which high pressure steam or hot water passes at the time of moist heat sterilization, and a frame of the pressing member is formed from a porous member through which steam or hot water passes. When plural sterilization trays are stacked in a state in which a resin container (multi-chamber container) 1 is placed on the sterilization tray, the peripheral edge of an empty chamber part of the resin container is pressed by the pressing member of the sterilization tray stacked above, and deformation of the resin container during the moist heat sterilization can be prevented.

16 Claims, 12 Drawing Sheets

(51) Int. Cl.
*A23L 3/00* (2006.01)
*A61J 1/10* (2006.01)

(56) References Cited

U.S. PATENT DOCUMENTS 5,910,138 A * 6/1999 Sperko ................. A61J 1/10
604/408
2007/0280044 A1 12/2007 Persoons et al.

FOREIGN PATENT DOCUMENTS

| | | |
|---|---|---|
| JP | 50-131886 U | 10/1975 |
| JP | 58-161814 U | 10/1983 |
| JP | 60-147298 U | 9/1985 |
| JP | 4-071605 U | 6/1992 |
| JP | 4-176465 A | 6/1992 |
| JP | 5-076297 U | 10/1993 |
| JP | 5-253276 A | 10/1993 |
| JP | 7-125779 A | 5/1995 |
| JP | 10-33643 A | 2/1998 |
| JP | 2000-50848 A | 2/2000 |
| JP | 2005-13537 A | 1/2005 |

OTHER PUBLICATIONS

Communication dated Sep. 27, 2016, issued by the European Patent Office in corresponding European Application No. 14860953.0.
International Preliminary Report on Patentability for PCT/JP2014/077514 dated Mar. 17, 2015.
International Search Report for PCT/JP2014/077514 dated Nov. 18, 2014.

* cited by examiner

STERILIZATION TRAY AND MOIST HEAT STERILIZATION METHOD

CROSS-REFERENCE TO RELATED APPLICATIONS

The present application is a Continuation of PCT International Application No. PCT/JP2014/077514 filed on Oct. 16, 2014 claiming priority under 35 U.S.C. § 119(a) to Japanese Patent Application No. 2013-229349 filed on Nov. 5, 2013. Each of the above applications is hereby expressly incorporated by reference, in their entirety, into the present application.

BACKGROUND OF THE INVENTION

1. Field of the Invention

The present invention relates to a sterilization tray and a moist heat sterilization method, and more particularly, the invention relates to a moist heat sterilization method for sterilizing a resin container filled with a medicine, food or the like using steam or hot water, and to a sterilization tray used for this method.

2. Description of the Related Art

In a case in which a resin container 1 such as an infusion solution bag as illustrated in FIG. 12 is subjected to moist heat sterilization, the resin container 1 is placed on a sterilization tray 2 and is put into a high pressure steam sterilization apparatus such as an autoclave, or a hot water spray type sterilization apparatus. Thus, the resin container 1 and the infusion fluid or the like inside the resin container are sterilized together by means of high pressure steam or hot water.

The resin container 1 illustrated in FIG. 12 is a multichamber container (double bag) in which a filled part 1a filled with an infusion solution and an empty chamber part 1b are divided by a partition part 1c, and after a sterilization treatment, the empty chamber part 1b is filled with a drug (a powder, a liquid or the like) and a gas barrier film may be attached thereto in order to protect the performance of the drug. Meanwhile, the multi-chamber container is not limited to a two-chamber container, and a three-chamber container and a four-chamber container are also available. Also, the sheet for the protection of performance is not limited to a gas barrier film, and an aluminum sheet, other sheets for making chambers for enclosing a desiccant or an oxygen scavenger, and the like are also available.

The bottom of the sterilization tray 2 is composed of a perforated plate (perforated metal) so that sterilization of the resin container 1 by means of high pressure steam or hot water, and dehydration and drying after sterilization can be facilitated. Meanwhile, a stopper part 1d of the resin container 1 is supported by a support 2a fixed to the bottom of the sterilization tray 2.

When moist heat sterilization is carried out in a state in which such a resin container 1 is placed on the sterilization tray 2, the resin container 1 is deformed as illustrated in FIGS. 13A and 13B, and there is a problem that creases are generated particularly in the peripheral edge of the resin container 1, or traces of the openings of the perforated plate (sterilization traces) 1e are produced.

When creases are generated in the peripheral edge or the like of the resin container 1, the attachment of the gas barrier film in the subsequent process is adversely affected. Furthermore, the sterilization traces 1e cause diffuse reflection of light at the time of performing an inspection if any foreign materials are present inside the resin container 1, and make it difficult to find foreign materials in the inside. Also, there is a problem that the sterilization traces 1e make characters, symbols and the like printed on the surface of the resin container 1 poorly visible.

There have been hitherto suggested the inventions described in JP 1992-176465A (JP-H04-176465A), JP 1993-253276A (JP-H05-253276A), JP 1998-33643A (JP-H10-33643A) and JP 1993-76297U (JP-H05-76297U) as sterilization trays that prevent deformation of this kind of resin containers.

In the invention described in JP 1992-176465A (JP-H04-176465A), buoyancy is imparted to the resin container by filling the inside of a water tank type tray with hot water, and thus the container itself being deformed under the weight of the content is prevented.

In the invention described in JP 1993-253276A (JP-H05-253276A), in order to prevent the resin container that has been subjected to a high pressure steam sterilization treatment from being deformed into a so-called semicylindrical shape (the bottom being flat-shaped, and the upper part being curved), the shape of the bottom face of the sterilization tray is made into the shape of the resin container, and thereby, the resin container is prevented from being deformed into a semicylindrical shape.

The invention described in JP 1998-33643A (JP-H10-33643A) is a swinging rotation type spray style retort sterilization method, in which when a product inside a pouch is heat sterilized by spraying and spouting steam or the like, the pouch is restrained to the tray by clamping the edge ear parts of the pouch with a pouch gripping member such as a clip mechanism or a bolt, and thus the movement of the pouch at the time of subjecting the tray to swinging rotation is prevented, or the occurrence of creases, pinholes and the like in the pouch is prevented.

In the invention described in JP 1993-76297U (JP-H05-76297U), in order to prevent curling or deformation occurring in the ear parts of a vacuum pack (material to be treated) of food as a result of a heating treatment, plural partitioning crosspieces are provided inside the tray by leaving an interval to the extent that the ear parts of both edges of the material to be treated can be placed, and a heating treatment is carried out such that when trays are superposed, the ear parts of the material to be treated are clamped between the upper part of the partitioning crosspieces and the bottom plate of a tray.

SUMMARY OF THE INVENTION

The sterilization tray described in JP 1992-176465A (JP-H04-176465A) is a water tank type tray filled with hot water (since a perforated plate is not used for the bottom plate), and therefore, there is no problem that sterilization traces are left on the resin container. However, this sterilization tray can be applied only to hot water sterilization, and cannot be used for the sterilization using high pressure steam.

The sterilization tray described in JP 1993-253276A (JP-H05-253276A) is such that the shape of the bottom face of the tray conforms to the shape of the resin container, and therefore, even after the resin container has been subjected to a high pressure moist heat treatment, the curved shape of the resin container that has swollen as a result of filling of a liquid medicine can be maintained. However, the suppression of deformation is limited only to the lower surface that is in contact with the tray due to the resin container's own weight, and for example, deformation of the peripheral edge of the resin container or the generation of creases cannot be prevented.

Furthermore, in regard to the invention described in JP 1998-33643A (JP-H10-33643A), since the pouch is restrained to the tray by clamping the edge ear parts of the pouch with a pouch gripping member such as a clip mechanism or a bolt, even if the tray is subjected to swinging rotation, the pouch can be prevented from moving on the tray, and the generation of creases at the edge ear parts of the pouch clamped with the pouch gripping member can be prevented. However, since the structure of the pouch gripping member is complex, the operation for gripping the pouch with the pouch gripping member becomes complicated, and there is a problem that sterilization of the edge ear parts of the pouch gripped by the pouch gripping member cannot be sufficiently carried out.

In regard to the sterilization tray described in JP 1993-76297U (JP-H05-76297U), since the ear parts of the material to be treated are clamped between the top part of partitioning crosspieces provided inside a tray and the bottom plate of a tray superposed on the top part, at least the material to be treated needs to be such that the surface including the ear parts is a flat surface. Thus, the shape of the material to be treated is limited. Furthermore, the pressing force changes with the total weight of the tray including the material to be treated, which is placed on top, and it is difficult to press the ear parts of all materials to be treated under the same conditions.

The present invention was achieved in view of such circumstances, and it is an object of the invention to provide a sterilization tray and a moist heat sterilization method, with which a resin container can be satisfactorily sterilized by means of steam or hot water and deformation of the resin container can be prevented.

In order to achieve the object described above, the sterilization tray related to an aspect of the invention comprises a tray having first voids through which at least steam or hot water passes at the time of moist heat sterilization, and having placed thereon a resin container filled with a liquid or a liquid mixed with a solid; and a pressing member having second voids through which at least steam or hot water passes at the time of moist heat sterilization, the pressing member pressing at least the peripheral edge of the resin container placed on the tray between the pressing member and the tray and preventing deformation of the resin container at the time of moist heat sterilization.

The tray on which a resin container is placed and the pressing member have first voids and second voids, respectively, through which at least steam or hot water passes, and form a structure that does not inhibit the sterilization action by causing steam or hot water to reach the resin container through these first voids and second voids. Furthermore, since the pressing member presses at least the peripheral edge of the resin container placed on the tray between the pressing member and the tray, the pressing member can prevent deformation of the resin container at the time of moist heat sterilization. Furthermore, since the pressing member has an ironing effect, flattening of the peripheral edge and the like of the resin container can be promoted even before the moist heat sterilization treatment.

In regard to the sterilization tray related to an embodiment of the invention, it is preferable that the tray is constructed from a perforated plate, wire gauze (preferably, metal wire gauze), or a porous member.

In regard to the sterilization tray related to another embodiment of the invention, it is preferable that the pressing member is constructed from a porous member, or from a porous member and a weight.

In regard to the sterilization tray related to another embodiment of the invention, it is preferable that the pressing member presses at least a region that is not filled with a liquid in the resin container.

In regard to the sterilization tray related to still another embodiment of the invention, it is preferable that the resin container has a filled part filled with a liquid or a liquid mixed with a solid; and an empty chamber part, and the region at which the resin container is pressed by the pressing member is the entire region of the empty chamber part or the peripheral edge of the empty chamber part. In a case in which the resin container is a multi-chamber container (double bag or the like) for infusion solution, the resin container is subjected to a sterilization treatment in a state in which the filled part is filled with an infusion solution, subsequently the empty chamber part is filled with a drug, and a gas barrier film or the like is attached thereto. However, since the entire region of the empty chamber part or the peripheral edge of the empty chamber part is pressed by the pressing member, and deformation thereof is prevented, attachment of the gas barrier film or the like can be satisfactorily carried out.

In regard to the sterilization tray related to still another embodiment of the invention, it is preferable that the tray is formed into a shape which is capable of being stacked in a state of accommodating a resin container, and the pressing member is attached in a direction perpendicular to the tray in a freely movable manner and presses a resin container accommodated in the tray placed immediately below at the time of stacking of trays.

By attaching the pressing member to the tray, the tray and the pressing member can be integrated, and the pressing member does not become an obstacle when resin containers are disposed side by side on the tray because the pressing member is not placed on the tray.

In regard to the sterilization tray related to still another embodiment of the invention, it is preferable that the pressing member has a biasing member between the pressing member and the tray, and a biasing force exerted by the biasing member is applied as the pressing force. Thereby, even if the pressing member is made lightweight, a desired pressing force can be obtained.

In regard to the sterilization tray related to still another member of the invention, it is preferable that the tray has a level difference between the bottom face on which the filled part of the resin container is placed and the bottom face on which the empty chamber part is placed, and the bottom face on which the empty chamber part is placed is formed to be higher by a height equivalent to one-half the height of the filled part than the bottom face on which the filled part of the resin container is placed. Thereby, the shape of the resin container after the sterilization treatment can be made symmetric, and a space for attaching the pressing member can also be secured below the tray.

In regard to the sterilization tray related to still another embodiment of the invention, it is preferable that the tray has an accommodation part that accommodates plural resin containers side by side, and plural pressing members are attached to the tray correspondingly to the plural resin containers accommodated in the tray and are independently attached to the tray in a freely movable manner. Thereby, pressing forces can be applied independently to each of plural resin containers, and an ironing effect (surface flattening) obtainable under the same conditions can be expected for all the resin containers.

In regard to the sterilization tray related to still another embodiment of the invention, a tray is preferable in which the bottom on which a resin container is placed is constructed from a perforated plate, the openings formed in the perforated plate are such that when the diameter, in a case in which the openings are round holes, or the minimum width, in a case in which the openings are long holes, is designated as the representative opening length, the representative opening length is from 0.3 mm to 3.3 mm, and the opening ratio of the perforated plate is from 2.5% to 15%. It has been found that the traces of openings (sterilization traces) of the perforated plate, which are left on the resin container after moist heat sterilization, are affected by the representative opening length and the opening ratio. Further, when the representative opening length was adjusted to a value of from 0.3 mm to 3.3 mm, and the opening ratio of the perforated plate was adjusted to a value of from 2.5% to 15%, sterilization traces were not left on the resin container after moist heat sterilization, or sterilization traces were unnoticeable.

In regard to the sterilization tray related to still another embodiment of the invention, it is preferable that the representative opening length is from 0.3 mm to 3 mm, and the opening ratio of the perforated plate is from 2.5% to 10%.

In regard to the sterilization tray related to still another embodiment of the invention, it is preferable that the representative opening length is from 0.8 mm to 1.5 mm, and the opening ratio of the perforated plate is from 4% to 8%.

According to another aspect of the invention, there is provided a moist heat sterilization method for sterilizing a resin container filled with a liquid or a liquid mixed with a solid, by means of steam or hot water, the method comprising a step of preparing a tray having first voids through which at least steam or hot water passes and a pressing member having second voids through which at least steam or hot water passes to place a resin container on the tray; a step of mounting a pressing member on the resin container on the tray to press at least the peripheral edge of the resin container between the pressing member and the tray; and a step of sterilizing the resin container in a pressed state by means of steam or hot water.

In regard to the moist heat sterilization method related to still another embodiment of the invention, it is preferable that during the pressing process, pressure is applied by the pressing member's own weight, pressure is applied by the pressing member's own weight and the weight placed on top of the pressing member, or pressure is applied by the pressing member's own weight and a biasing member that urges the pressing member from the top.

According to the invention, as the tray and the pressing member, a tray and a pressing member respectively having voids through which at least steam or hot water passes are used, and the pressing member presses at least the peripheral edge of a resin container placed on the tray between the pressing member and the tray. Therefore, the moist heat sterilization action on the resin container can be prevented from being inhibited, and at the time of moist heat sterilization, the resin container can be prevented from being deformed.

DESCRIPTION OF THE PREFERRED EMBODIMENTS

Hereinafter, preferred embodiments of the sterilization tray and the moist heat sterilization method related to the present invention will be explained with reference to the attached drawings.

First Exemplary Embodiment

Figure 1:
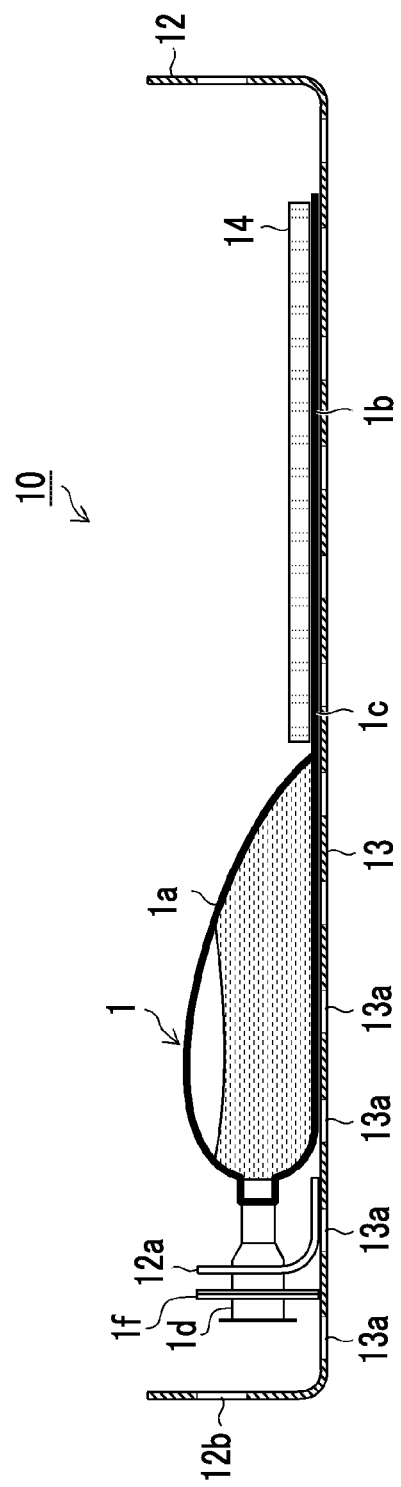
FIG. 1 is a lateral cross-sectional view diagram illustrating a first exemplary embodiment of the sterilization tray related to the invention.

FIG. 1 is a lateral cross-sectional view diagram illustrating a first exemplary embodiment of the sterilization tray related to the invention.

The sterilization tray 10 illustrated in FIG. 1 is composed of a tray 12 and a pressing member 14.

The tray 12 is intended for moist heat sterilization of a resin container (in the present example, a multi-chamber container (double bag)) 1 filled with a liquid, and the tray has an accommodation part that accommodates plural resin containers 1 side by side. Plural resin containers 1 are placed thereon side by side on the bottom.

The resin containers 1 placed on the tray 12 are introduced into a high pressure steam sterilizer together with the tray 12 and are subjected to high pressure steam sterilization (autoclave sterilization). In the present example, sixty-three (=7× 9) resin containers 1 are arranged in one tray 12, and thirty-three trays 12 are stacked. Thus, sterilization is carried out at a ratio of 2079 resin containers/batch.

Figure 12:
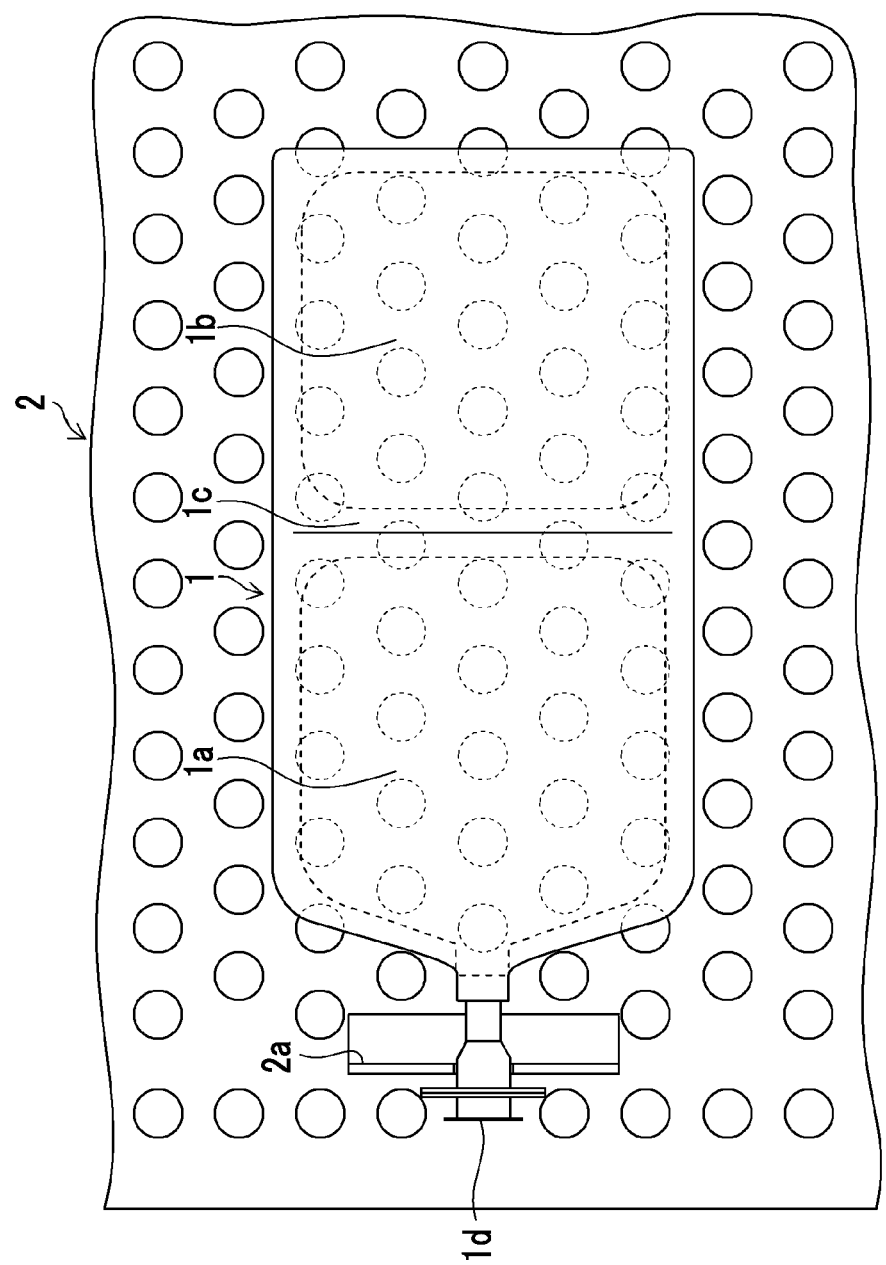
FIG. 12 is a plan view diagram of essential parts illustrating an example of a conventional sterilization tray.
Figure 13A:
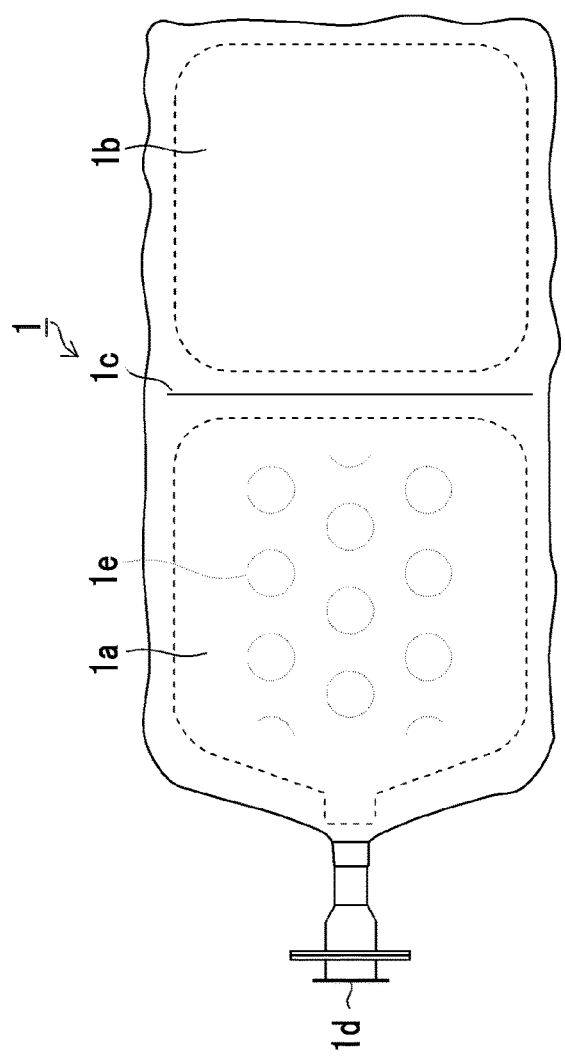
FIGS. 13A and 13B are diagrams illustrating a resin container that has been moist heat sterilized using the sterilization tray illustrated in FIG. 12.
Figure 13B:
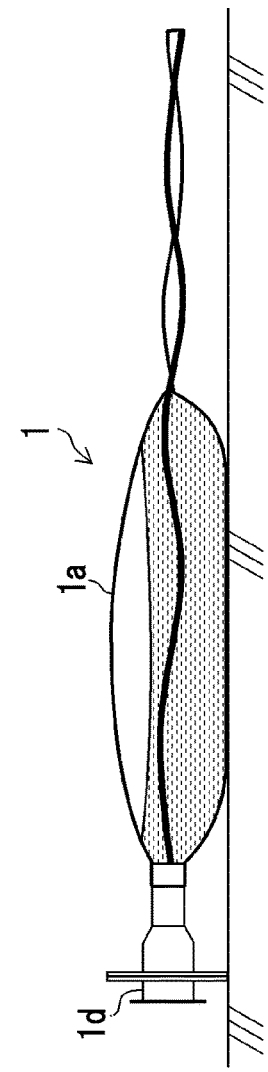

A resin container 1 is constructed from a resin film of a polyethylene resin, a polypropylene resin or the like, and as explained in FIG. 12 and FIG. 13, a resin container 1 to be moist heat sterilized has a filled part 1$a$ filled with an infusion solution such as physiological saline; and an empty chamber part 1$b$ that is to be filled with a drug such as a powder or a liquid after moist heat sterilization. The peripheral edge of the resin container 1 is welded by heat sealing, and a partition 1c between the filled part 1a and the empty chamber part 1b has easy-to-peel openability provided by weak sealing. By opening the partition 1c, an infusion solution and a drug can be mixed in an aseptic state.

As illustrated in FIG. 1, the bottom of the tray 12 is provided with a support 12a that supports a stopper part 1d of the resin container 1 at a certain level, and on the lateral side of the tray 12, openings 12b through which high pressure steam, hot water, and air (drying/cooling air) pass are formed. Meanwhile, as illustrated in FIG. 1, the stopper part 1d may be adjusted to be at a certain level by providing a port flange if of the stopper part 1d into an appropriate size, and bringing the port flange if into contact with the bottom of the tray 12. In this case, the support 12a functions as a position determining means for determining the position of the stopper part 1d (resin container 1) on the tray 12.

Furthermore, the bottom of the tray 12 is composed of a perforated plate (perforated metal) 13 having formed thereon openings (first voids) 13a through which high pressure steam or hot water passes.

The pressing member 14 is placed as a stone weight on top of a resin container 1 as illustrated in FIG. 1. The pressing member 14 presses the resin container 1 in a state in which the entire region or the peripheral edge of the empty chamber part 1b of the resin container 1 is interposed between the pressing member 14 and the perforated plate 13 at the bottom of the tray 12.

This pressing member 14 is composed of a flat plate formed from a porous member (a porous metal, a porous ceramic or the like) having second voids through which high pressure steam or hot water passes. Meanwhile, the pressing member 14 is not limited to a porous member, and may also be constructed from wire gauze or a perforated plate.

The resin container 1 placed on the perforated plate 13 of the sterilization tray 10 has its empty chamber part 1b interposed between the perforated plate 13 and the pressing member 14 and pressed by the pressing member 14's own weight. Thereby, the resin container 1 can be prevented from being deformed at the time of moist heat sterilization.

Furthermore, since the pressing member 14 is constructed from a porous member through which high pressure steam or hot water passes, the pressing member 14 does not inhibit sterilization of the empty chamber part 1b of the resin container 1.

The resin container 1 that has been moist heat sterilized as such is thereafter subjected to introduction of a drug into the empty chamber part 1b, and a gas barrier film is attached thereto in order to protect the performance of the drug. However, since the resin container 1 is prevented from being deformed at the time of moist heat sterilization, attachment of the gas barrier film can be carried out satisfactorily.

The condition of deformation of the resin container 1 caused by the presence or absence of the pressing member 14 at the time of moist heat sterilization, and the presence or absence of leakage upon the attachment of the gas barrier film were checked. The results are presented in Table 1.

TABLE 1

| Pressing member | Deformation of resin container 1 | Gas barrier film attachment |
|---|---|---|
| Absent | Large | Leakage occurs in some containers |
| Present | Very small | No leakage |

As shown in [Table 1], when the resin container 1 is pressed by means of the pressing member 14, deformation of the resin container 1 can be suppressed, compared to the case in which the pressing member 14 is not used. As a result, attachment of the gas barrier film could be carried out satisfactorily, and leakage of gas could be prevented.

First Modification Example of First Exemplary Embodiment

Figure 2:
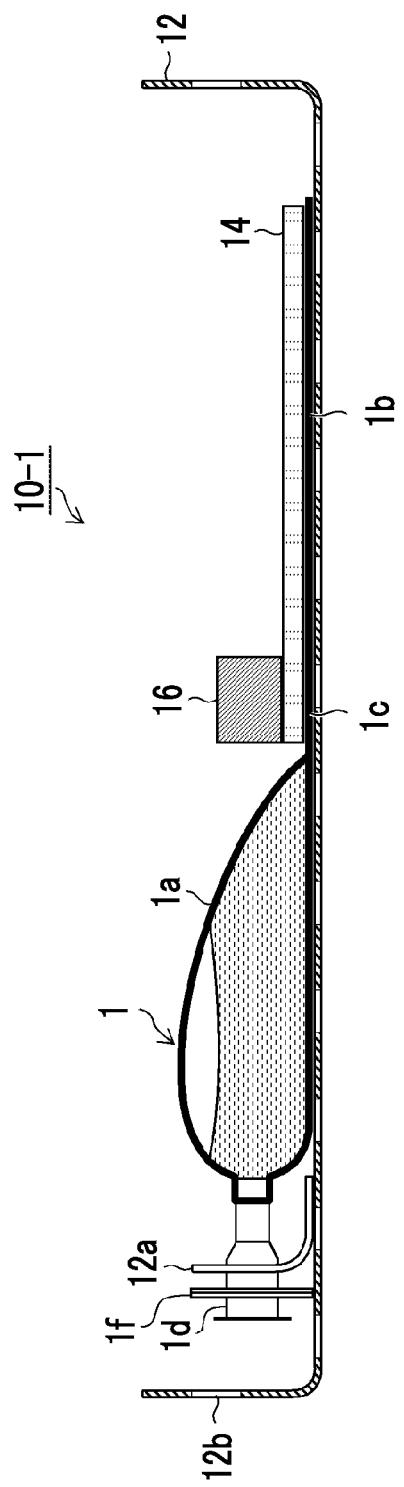
FIG. 2 is a lateral cross-sectional view diagram illustrating a first modification example of the first embodiment of the sterilization tray related to the invention.

FIG. 2 is a lateral cross-sectional view diagram illustrating a first modification example of the first exemplary embodiment of the sterilization tray related to the invention. Meanwhile, in FIG. 2, the same symbols are assigned to the parts that are common with the parts in the sterilization tray 10 illustrated in FIG. 1, and detailed explanations thereof will not be given here.

The sterilization tray 10-1 illustrated in FIG. 2 is different from the sterilization tray 10 illustrated in FIG. 1 in that a weight 16 has been added.

The weight 16 is an object placed as a stone weight on top of the pressing member 14, and is placed at a position corresponding to the partition (easy-to-peel seal) 1c between the filled part 1a and the empty chamber part 1b of the resin container 1.

When the weight 16 is placed on the pressing member 14, the pressing force is further added by the weight 16 so that the empty chamber part 1b (pressing member 14) is not lifted up by the expansion of air in the filled part 1a of the resin container 1 at the time of high pressure steam sterilization.

Second Modification Example of First Exemplary Embodiment

Figure 3:
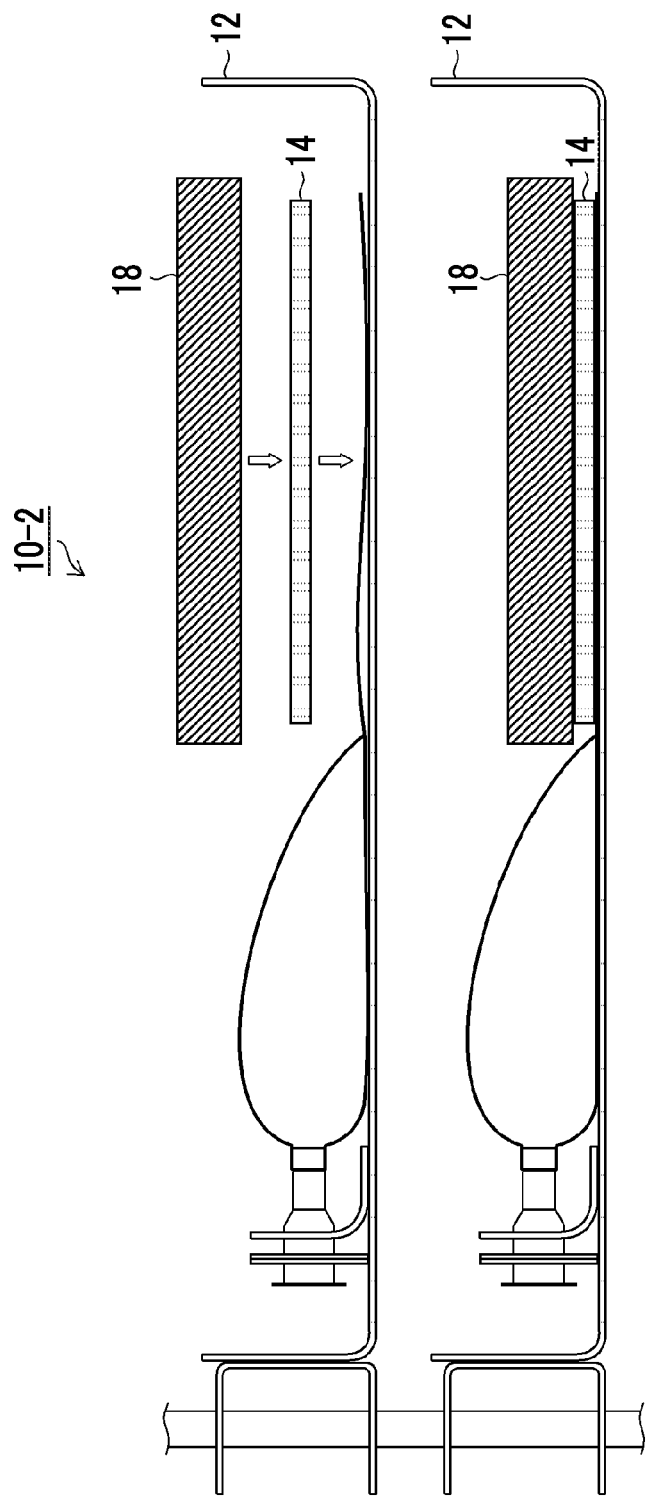
FIG. 3 is a lateral cross-sectional view diagram illustrating a second modification example of the first embodiment of the sterilization tray related to the invention.
Figure 4:
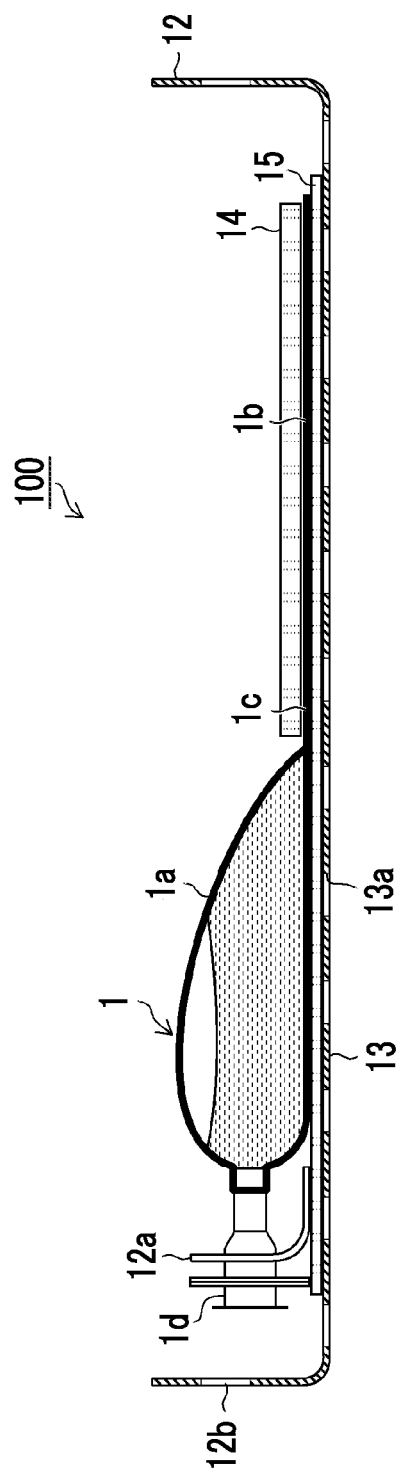
FIG. 4 is a lateral cross-sectional view diagram illustrating a second exemplary embodiment of the sterilization tray related to the invention.

FIG. 3 is a lateral cross-sectional view diagram illustrating a second modification example of the first exemplary embodiment of the sterilization tray related to the invention. Meanwhile, in FIG. 3, the same symbols are assigned to the parts that are common with the parts in the sterilization tray 10 illustrated in FIG. 1, and detailed explanations thereof are not given here. Furthermore, FIG. 4 shows the case in which two trays 12 are stacked.

The sterilization tray 10-2 illustrated in FIG. 3 is different from the sterilization tray 10 illustrated in FIG. 1 in that a weight 18 has been added.

The weight 18 is an object placed as a stone weight on top of the pressing member 14, and has a size which uniformly presses the entirety of the pressing member 14.

When the weight 18 is placed on the pressing member 14, the pressing forces exerted by the respective weights of the weight 18 and the pressing member 14 themselves can be evenly applied to the resin container 1. By using the weight 18 as such, the pressing member 14 can be made lightweight (thin), or a relatively lightweight material can be selected as the porous material that constitutes the pressing member 14.

In the first and second modification examples of the first exemplary embodiment described above, the pressing member 14 and the weight 16 or 18 are separated; however, the pressing member 14 and the weight 16, or the pressing member 14 and the weight 18 may be integrated.

Second Exemplary Embodiment

Figure 5:
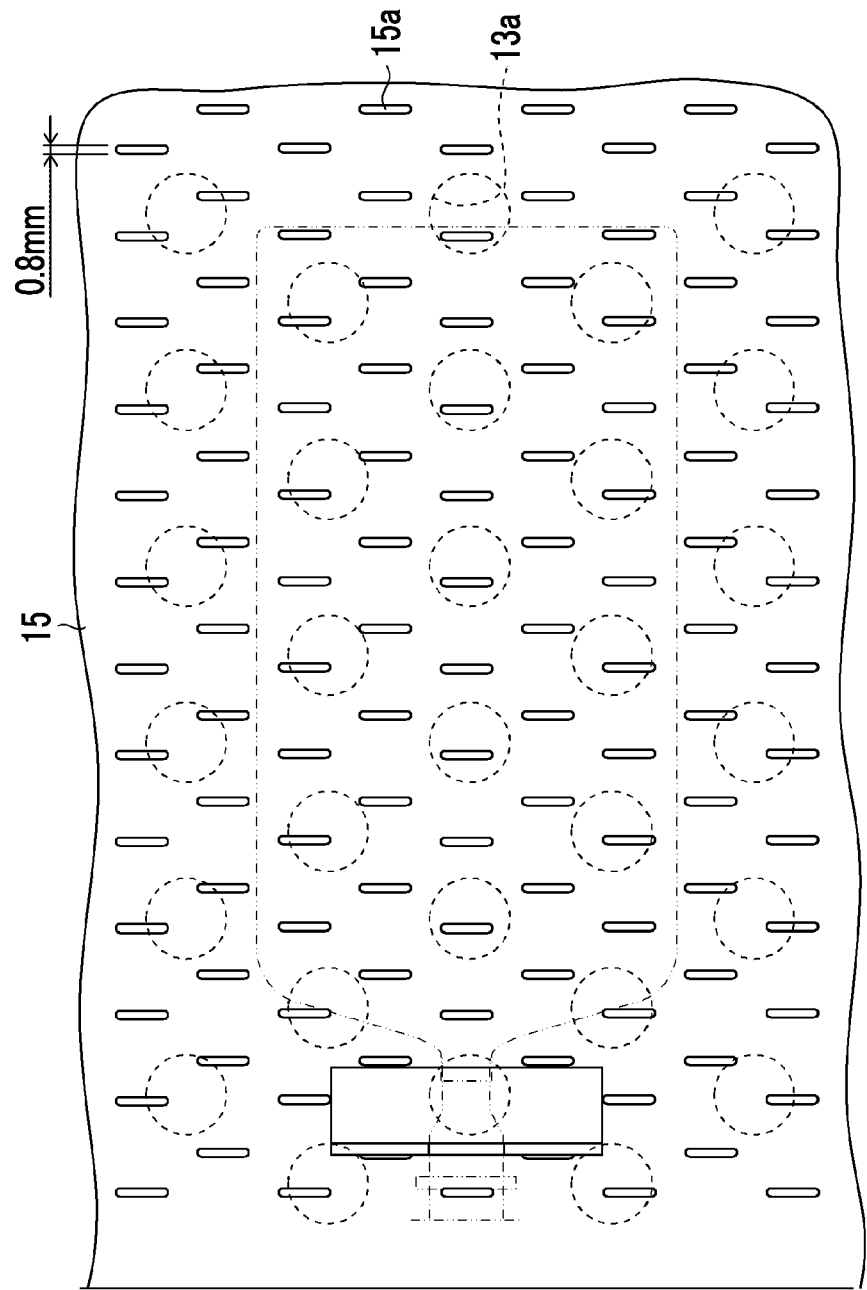
FIG. 5 is a plan view diagram of essential parts of the tray illustrated in FIG. 4.

FIG. 4 is a lateral cross-sectional view diagram illustrating a second exemplary embodiment of the sterilization tray related to the invention, and FIG. 5 is a plan view diagram of essential parts of the sterilization tray illustrated in FIG. 4. Meanwhile, in FIG. 4, the same symbols are assigned to the parts that are common with the parts in the sterilization tray 10 illustrated in FIG. 1, and detailed explanations thereof are not given here.

The sterilization tray 100 illustrated in FIG. 4 is different from the sterilization tray 10 illustrated in FIG. 1 in that a perforated plate 15 is laid on the bottom (perforated plate 13) of the sterilization tray 10.

The bottom (perforated plate 13) of the sterilization tray 10 has, for example, openings 13a of round holes (see FIG. 5) having a diameter of ϕ10 mm (wherein ϕ is the symbol representing the hole diameter) formed thereon; however, in the sterilization tray 100, a perforated plate 15 having slit-like openings 15a is laid on this perforated plate 13.

<Perforated Plate 15>

In order to solve the problem that traces of the openings of the perforated plate (sterilization traces) are left on the surface of the resin container after moist heat sterilization, an investigation was conducted on the way in which sterilization traces are produced under various conditions such as the shape and the size of the openings formed on the perforated plate, and the opening ratio.

Here, in a case in which the openings formed on the perforated plate are round holes, the diameter of the round holes is designated as the representative opening length, and in the case of long holes (slit holes), the minimum width of the long holes is designated as the representative opening length.

Figure 6:
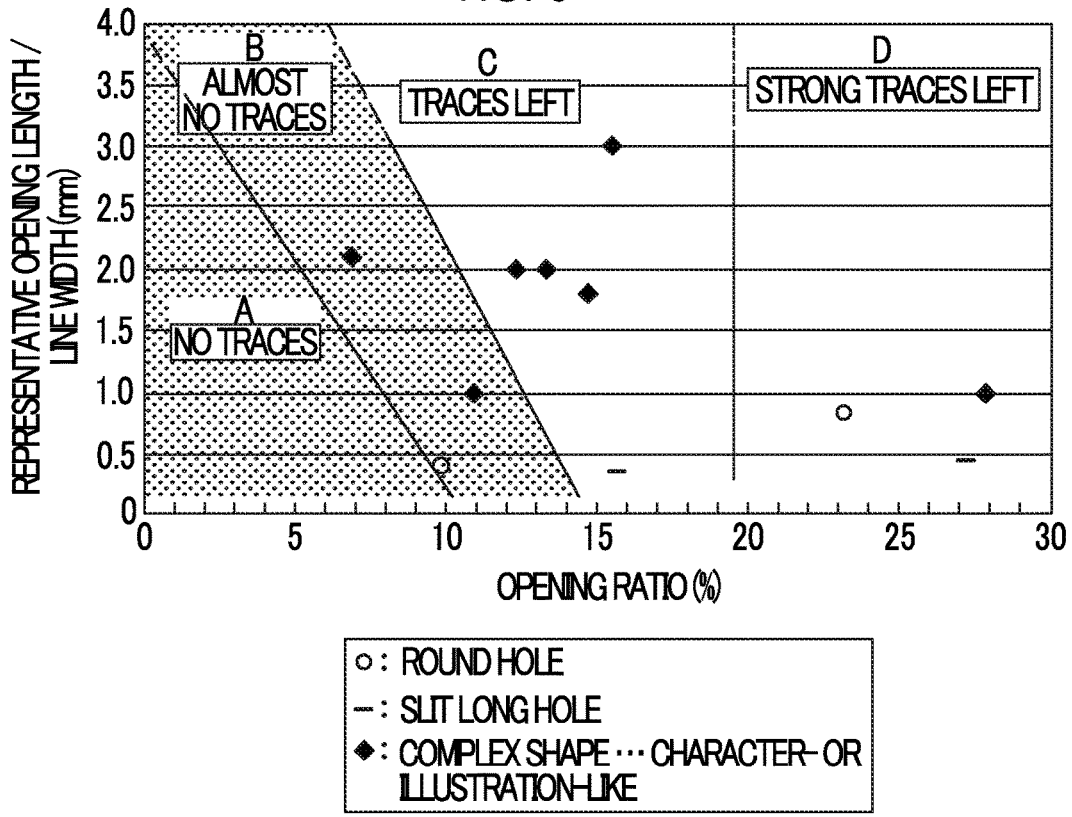
FIG. 6 is a graph showing the distribution of the intensities of sterilization traces left on the surface of a resin container.

FIG. 6 is a graph illustrating the distribution of the intensities of sterilization traces left on the surface of a resin container in a case in which the opening ratio (%) and the representative opening length of the openings formed on the perforated plate are changed. Meanwhile, the horizontal axis of the graph in FIG. 6 represents the opening ratio (%), and the vertical axis represents the representative opening length. Furthermore, in the graph of FIG. 5, o (the white circle mark) represents the perforated plate with round holes, - (the bar mark) represents the perforated with slit long holes, and ♦ (the black diamond mark) represents the perforated plate holes having complicated shapes (character or illustration-like).

As illustrated in the graph of FIG. 6, in a case in which the opening ratio and the representative opening length of the openings formed on the perforated plate belonged to region A, no traces of the openings of the perforated plate (sterilization traces) were left on the surface of the resin container, and in a case in which the opening ratio and the representative opening length belonged to region B, there were almost no sterilization traces left. In a case in which the opening ratio and the representative opening length belonged to region C, sterilization traces were left, and in a case in which the opening ratio and the representative opening length belonged to region D, strong sterilization traces were left.

As a result of this investigation, it was found that, in regard to the way in which sterilization traces are left, the influence of the opening ratio is larger than the influence of the representative opening length, unlike what had been expected originally.

On the other hand, regarding the conditions with which the opening ratio (%) and the representative opening length of the opening formed on the perforated plate are determined, it is necessary to consider the ease of performing an inspection of the resin container, the ease of drying (dehydration) of the perforated plate, and the ease of processing of the openings to be formed on the perforated plate, in accordance with the intensity of the sterilization traces left on the surface of the resin container.

Figure 7:
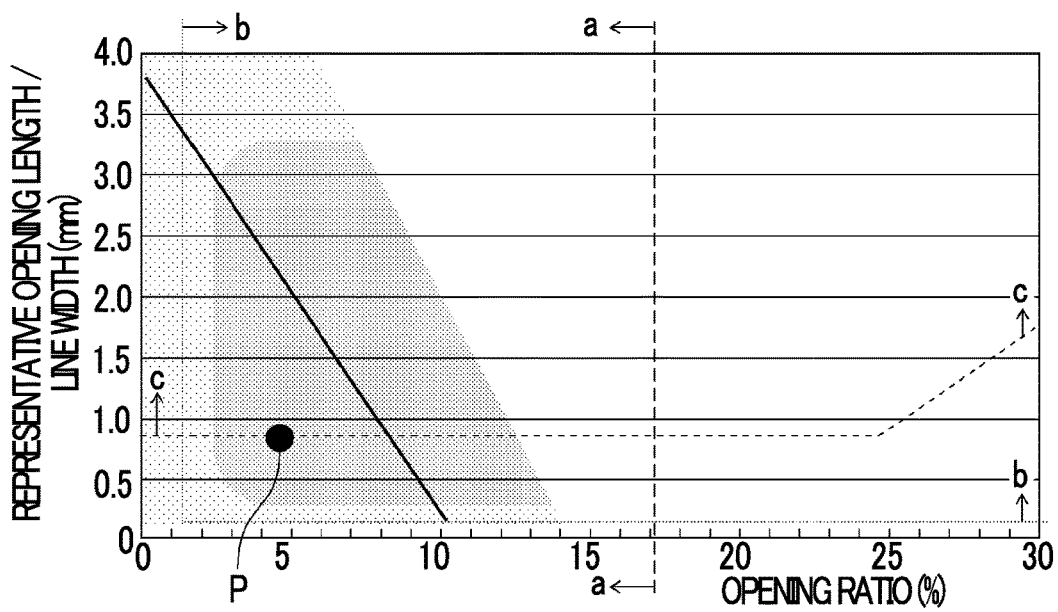
FIG. 7 is a graph showing a region a for easy inspection, a region b for easy drying, and a region c for easy processing, on the graph illustrated in FIG. 6.

FIG. 7 is a graph showing a region a for easy inspection, a region b for easy drying, and a region c for easy processing, on the graph shown in FIG. 6. The region c for easy processing is a region in which a sterilization tray can be produced without incurring costs, and currently, with a length of 0.8 mm or more, sterilization trays can be produced at low cost.

From the viewpoint described above, a region which belongs to regions A and B in the graph of FIG. 6, and overlaps with regions a, b and c in the graph of FIG. 7, was designated as a "feasible region" for the opening ratio (%) and the representative opening length of the openings formed on the perforated plate. That is, a range in which the representative opening length is from 0.3 mm to 3.3 mm and the opening ratio is from 2.5% to 15%, was designated as the "feasible region".

Furthermore, a region which belongs to region A in the graph of FIG. 6 and belongs to regions a, b and c in the graph of FIG. 7, that is, a range in which the representative opening length is from 0.3 mm to 3 mm and the opening ratio is from 2.5% to 10%, is more preferred.

Furthermore, a range in which the representative opening length is from 0.8 mm to 1.5 mm and the opening ratio is from 4% to 8%, is most preferred.

The slit-like openings 15a formed on the perforated plate 15 illustrated in FIG. 5 corresponds to the position P on the graph of FIG. 7, and has a representative opening length of 0.8 mm and an opening ratio of 4.6%, which are within the most preferred range.

In general, since the limit of the representative opening length is the plate thickness, when 0.8 mm is selected as the representative opening length, the plate thickness of the perforated plate should be 0.8 mm or less. Meanwhile, in commercially available perforated plates, ϕ0.8 mm is the minimum value.

Since a perforated plate having a plate thickness of 0.8 mm or less has insufficient strength, the perforated plate cannot be used as received, as the bottom of the sterilization tray.

As illustrated in FIG. 4, the sterilization tray 100 of the second exemplary embodiment has a perforated plate 15 having slit-like openings 15a (having a representative opening length of 0.8 mm) (FIG. 5) laid on a perforated plate 13 having sufficient strength.

Thereby, sterilization traces being left on the resin container 1 after moist heat sterilization can be prevented.

Meanwhile, instead of the perforated plate 15 laid on the bottom of the sterilization tray 100, it is acceptable to lay a wire gauze, a porous member or the like so that no sterilization traces are left.

Third Exemplary Embodiment

Figure 8:
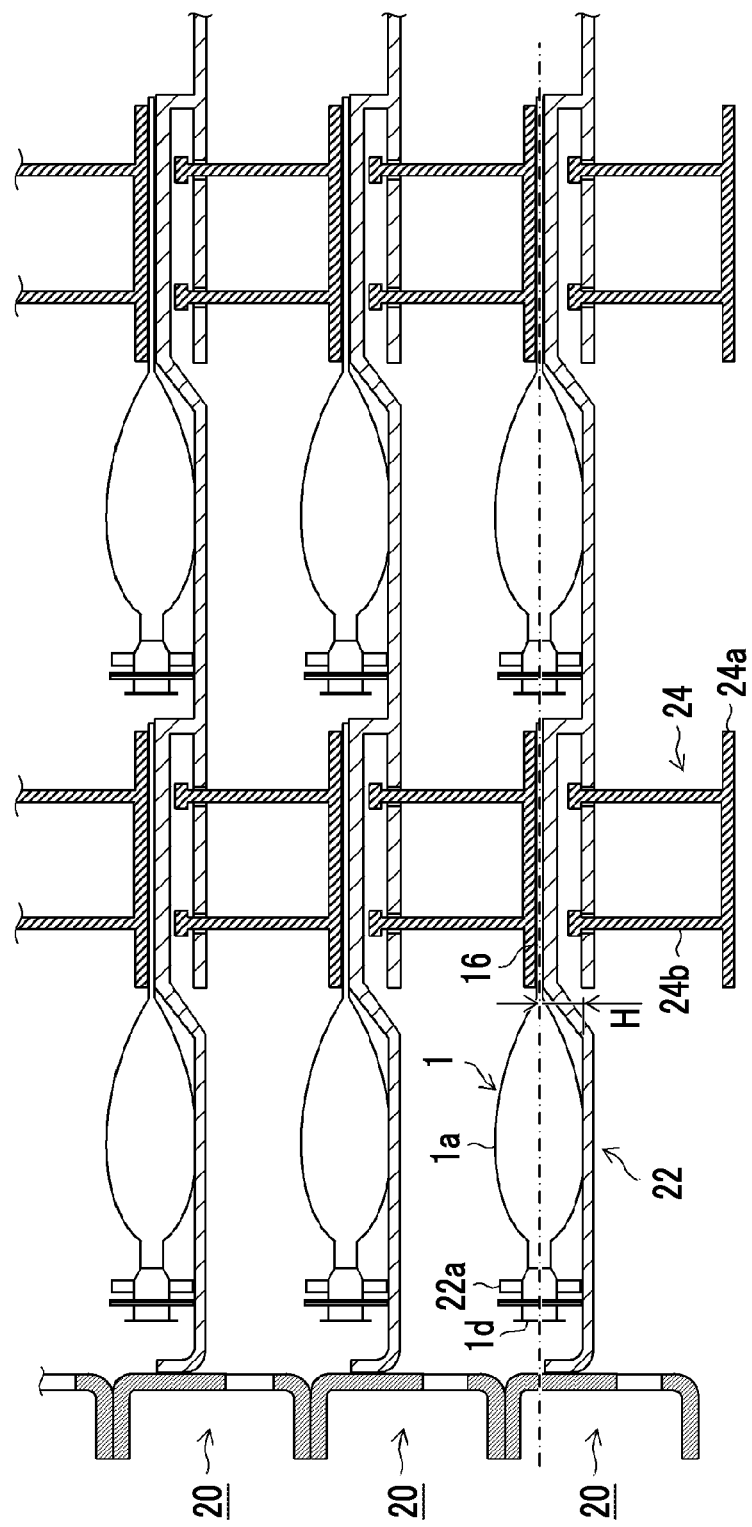
FIG. 8 is a lateral cross-sectional view diagram illustrating a third exemplary embodiment of the sterilization tray related to the invention.
Figure 9:
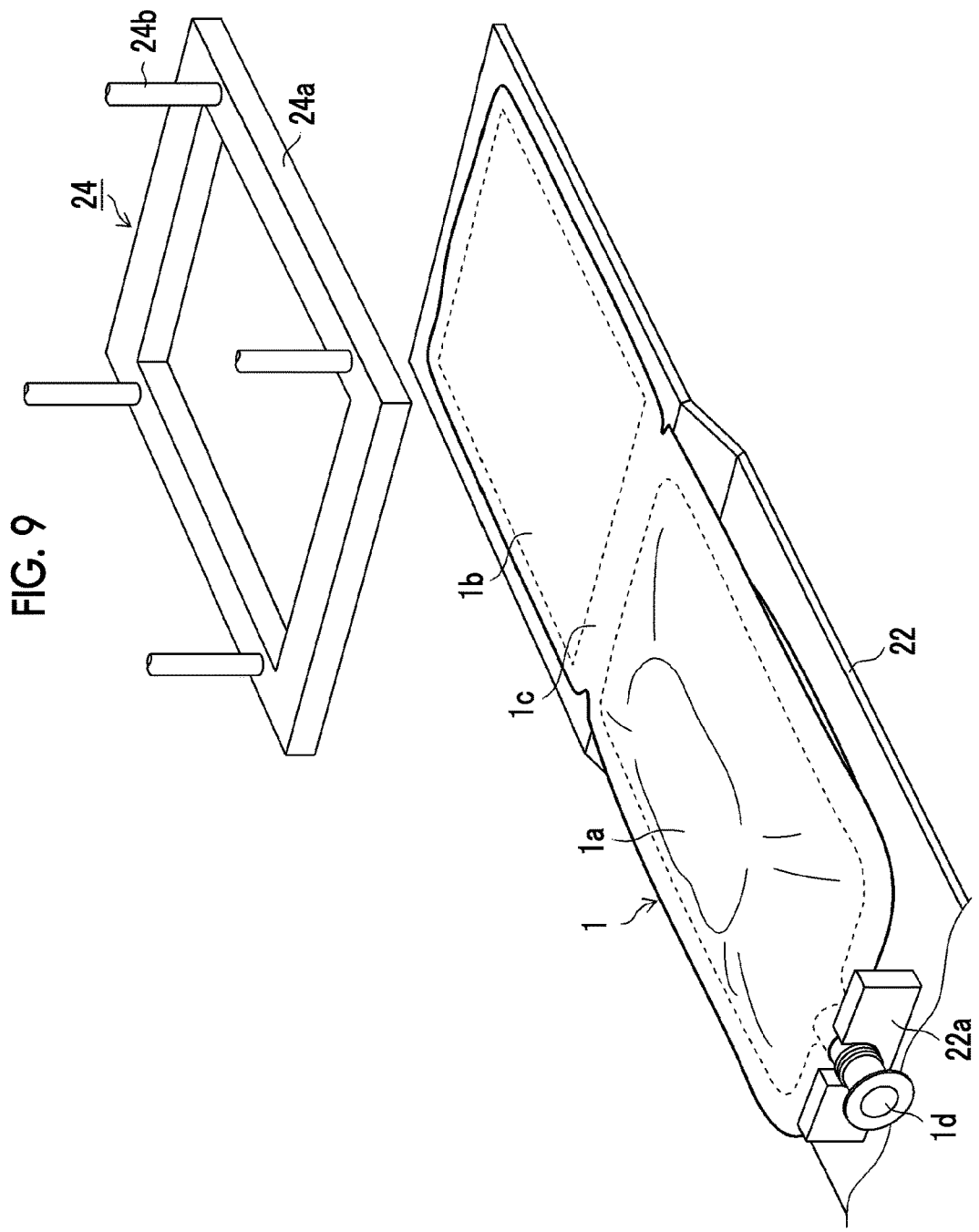
FIG. 9 is a perspective view diagram of essential parts of the sterilization tray illustrated in FIG. 8, and is a diagram illustrating the state before pressing of a resin container.

FIG. 8 is a lateral cross-sectional view diagram illustrating a third exemplary embodiment of the sterilization tray related to the invention, and FIG. 9 is a perspective view diagram of essential parts of the sterilization tray illustrated in FIG. 8. Meanwhile, FIG. 8 shows the state in which plural sterilization trays 20 are stacked.

The sterilization tray 20 illustrated in FIG. 8 is composed of a tray body (tray) 22 and a pressing member 24.

The tray body 22 is intended for implementing moist heat sterilization of resin containers 1, and the resin containers 1 are placed thereon side by side on the bottom.

The tray body 22 is formed into a shape that can be stacked in a state of accommodating resin containers 1, and as illustrated in FIG. 9, the tray body 22 is provided with a support 22a that supports the stopper part 1d of a resin container 1.

The bottom of the tray body 22 has a level difference H between the bottom face on which the filled part 1a of the resin container 1 is placed, and the bottom face on which the empty chamber part 1b of the resin container 1 is placed. In other words, the bottom on which the empty chamber part 1b is placed is formed to be higher by the level difference H than the bottom face on which the filled part 1a is placed. This level difference H corresponds to a height equivalent to one-half the height of the filled part 1a of the resin container 1. Meanwhile, the bottom of the tray body 22 is composed of the same shaped perforated plate as the perforated plate 13, as illustrated in FIG. 2.

Furthermore, the support 22a provided in the tray body 22 supports the stopper part 1d of the resin container 1 such that the height of the center of the stopper part 1d is equivalent to one-half the height of the filled part 1a.

Thereby, the resin container 1 placed on the tray body 22 becomes symmetrical in the vertical direction with respect to the center line of the resin container. Meanwhile, the level difference H of the bottom of the tray body 22 is not limited to the case in which the level difference H corresponds to a height equivalent to exactly one-half the height of the filled part 1a of the resin container 1, and when the level difference H is adjusted to a height equivalent to approximately one-half the height of the filled part 1a, the resin container 1 can be maintained to be approximately symmetrical in the vertical direction with respect to the center line of the resin container 1.

On the other hand, the pressing member 24 is attached in a direction perpendicular to the tray body 22 in a freely movable manner, and is integrated with the tray body 22.

As illustrated in FIG. 9, the pressing member 24 is composed of a frame 24a and four spindles 24b fixed to the frame 24a, and the upper ends of the spindles 24b are connected to the tray body 22 in a freely movable manner. The number of the spindles 24b is not limited to 4, and the number may also be 2 or 3.

The frame 24a of the pressing member 24 is formed from a porous material (porous metal) and has a shape corresponding to the peripheral edge (area including the peripheral edge that is welded by heat sealing and the partition 1c) of the empty chamber part 1b of the resin container 1.

Figure 10:
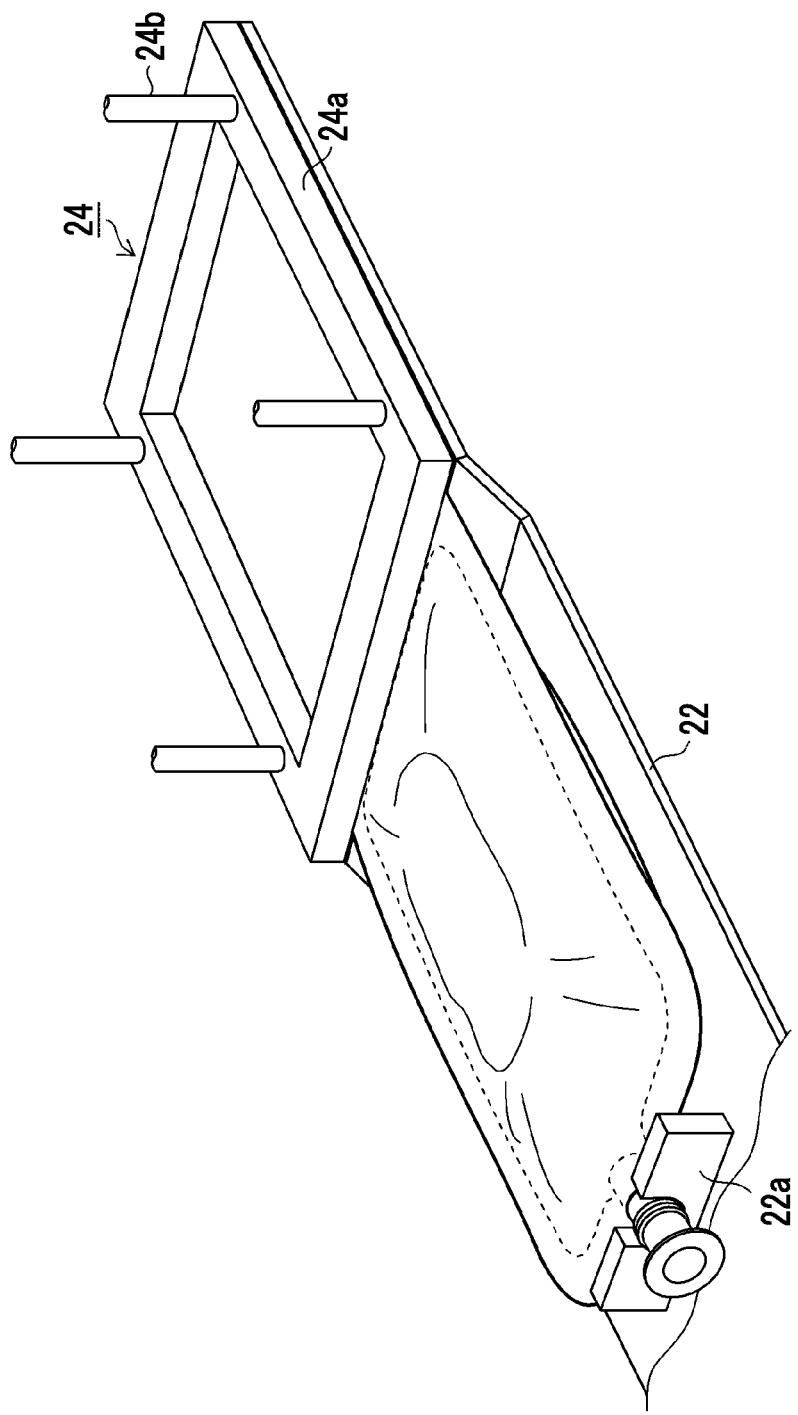
FIG. 10 is a perspective view diagram of essential parts of the sterilization tray illustrated in FIG. 8, and is a diagram illustrating the state during pressing of a resin container.

FIG. 10 is a perspective view diagram of essential parts of the sterilization tray illustrated in FIG. 8, and shows a state in which the peripheral edge of the empty chamber part 1b of the resin container 1 is pressed by the pressing member 24. Meanwhile, the pressing member 24 that presses the resin container 1 is the one installed in the sterilization tray 20 stacked over the sterilization tray 20 accommodating the relevant resin container 1.

The sterilization tray 20 having the configuration described above is such that the trays are stacked in a state of accommodating the resin containers 1 as illustrated in FIG. 10; however, the pressing member 24 of a sterilization tray 20 presses the peripheral edge of the empty chamber part 1b of the resin container 1 placed on the sterilization tray 20 immediately therebelow, only by means of the pressing member 24's own weight.

Furthermore, in one sterilization tray 20, the same number of pressing members 24 as the number of the resin containers 1 accommodated in the sterilization tray 20 (63 in the present example) are installed.

In the present example, twenty-one (=3×7) resin containers 1 were arranged in one sterilization tray 20, thirty-four sterilization trays 20 were stacked (one load), and three loads of these were subjected to moist heat sterilization. Meanwhile, resin containers 1 were not accommodated in the sterilization tray 20 of the topmost layer of the thirty-four trays, and this sterilization tray was caused to function as pressing means.

When the sterilization tray 20 of the second exemplary embodiment was used, the following operating effects were obtained.

(1) Since the sterilization tray 20 has the pressing member 24 integrated with the tray, and the empty chamber part 1b of the resin container 1 can be pressed only by superposing the sterilization trays 20, existing facilities can be used without any modification. There was available a conveyance apparatus by which sterilization trays with resin containers placed therein can be superposed and sterilized at a ratio of 2079 trays/batch and the trays can be sent to the subsequent process one at a time, and the basic design of the conveyance apparatus could be used without any modification.

(2) In the case of the sterilization tray 10 of the first exemplary embodiment, at the time of moist heat sterilization, the weight of the pressing member 14 (pressing member 14+weight) needed to be about 450 g ($\approx 8$ g/cm$^2$) so that the empty chamber part 1b (pressing member 14) would not be lifted up by the expansion of air in the filled part 1a of the resin container 1. However, as illustrated in FIG. 8, since the bottom of the tray body 22 was provided with a level difference H so as to prevent displacement of the empty chamber 1b (exertion of a force capable of lifting up the empty chamber part 1b) even if the filled part 1a of the resin container 1 expanded, the weight of the pressing member 24 could be set to about 250 g (4.5 g/cm$^2$).

Weight reduction of the pressing member 24 has an effect of reducing the running cost required when metal members other than manufactured products are heated to 105° C. to 121° C. or cooled to 50° C.

(3) Furthermore, as illustrated in FIG. 8, when the bottom of the tray body 22 is provided with a level difference H and the stopper part 1d of the resin container 1 is maintained at a certain height, the resin container 1 placed on the tray body 22 can be made symmetrical in the vertical direction with respect to the center line of the resin container 1, and the resin container 1 after sterilization can be maintained to have a symmetrical shape. Thereby, handleability in the subsequent processes is enhanced, and deterioration of the appearance does not occur.

(4) Plural pressing members 24 integrated with the tray body 22 can be each independently moved with respect to the tray body 22, and when a pressing member 24 is placed on the empty chamber part 1b of the resin container 1, the contact between the pressing member 24 and the tray body 22 is separated off. Also, since the sterilization tray has a structure in which one pressing member 24 is placed on one resin container 1, even if the tray body 22 is distorted, the pressing force exerted by the pressing member 24's own weight, which is applied to each resin container 1, becomes uniform.

(5) Since the same perforated plate as the perforated plate 15 illustrated in FIG. 5 (a perforated plate of the slit-like openings 15a having a representative opening length of 0.8 mm and an opening ratio of 4.6%) was used on the bottom of the tray body 22, sterilization traces were prevented from being left on the resin container 1 after moist heat sterilization.

(6) In the resin container 1, since the peripheral edge is welded by heat sealing through stamping with a heat sealer, the flatness of the peripheral edge is not uniform due to thermal shrinkage. However, since high pressure steam sterilization is performed in a state in which the peripheral edge of the empty chamber part 1b of the resin container 1 is interposed between the pressing member 24 and the bottom face of the tray body 22 (pressed state), there is an ironing effect of flattening the peripheral edge, and flattening of the peripheral edge of the resin container 1 could be promoted even compared to the state before the high pressure steam sterilization. Thereby, when the empty chamber part 1b of the resin container 1 is filled with a drug (a powder, a liquid or the like) after sterilization, and a gas barrier film is attached to the peripheral edge of the resin container 1 in order to protect the performance of the drug, the gas barrier film could be attached such that leakage at the peripheral edge would not occur.

Meanwhile, the pressing member 24 has a frame 24a that presses only the peripheral edge of the empty chamber part 1b of the resin container 1; however, the pressing member may also be formed into a flat plate instead of the frame 24a so that the entirety of the empty chamber part 1b can be pressed.

Modification Example of Third Exemplary Embodiment

Figure 11:
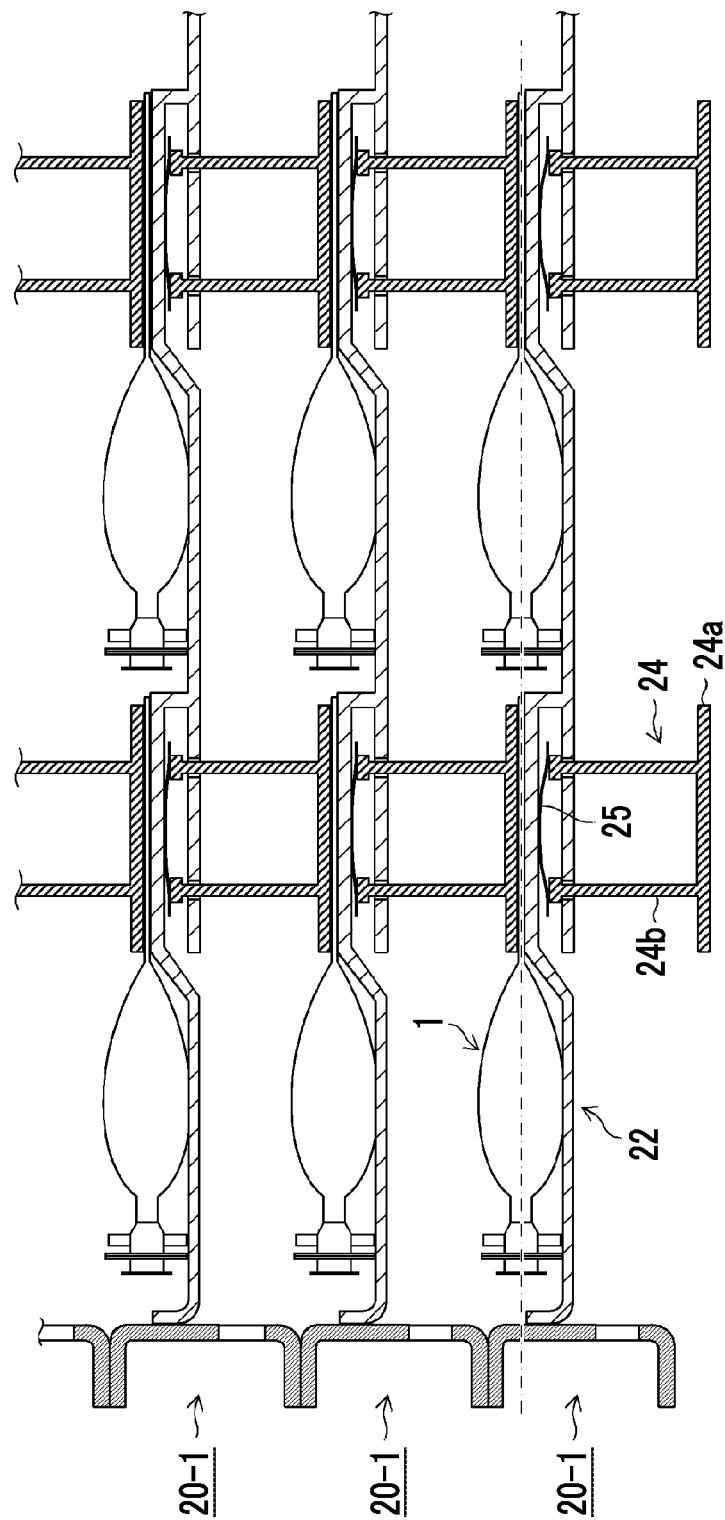
FIG. 11 is a lateral cross-sectional view diagram illustrating a modification example of the third exemplary embodiment of the sterilization tray related to the invention.

FIG. 11 is a lateral cross-sectional view diagram illustrating a modification example of the third exemplary embodiment of the sterilization tray related to the invention. In FIG. 11, the same symbols are assigned to the parts that are common with the parts in the sterilization tray 20 illustrated in FIG. 8, and detailed explanations thereof are not given here.

The sterilization tray 20-1 illustrated in FIG. 11 is different from the sterilization tray 20 illustrated in FIG. 8 in that a plate spring 25 has been added.

The plate spring 25 is provided between the tray body 22 and the upper end of the spindles 24b of the pressing member 24, and the plate spring 25 constantly exerts a biasing force in the direction in which the pressing member 24 is moved downward, on the pressing member 24. Therefore, when the pressing member 24 is placed on the empty chamber part 1b of the resin container 1, and the contact between the pressing member 24 and the tray body 22 is separated (slightly lifted up), the biasing force of the plate spring 25 is exerted on the empty chamber part 1b of the resin container 1 through the pressing member 24. That is, the biasing force of the plate spring 25 and the pressing member 24's own weight are applied to the empty chamber part 1b of the resin container.

Thereby, even if the weight of the pressing member 24 is reduced, a desired pressing force can be obtained. Furthermore, there is an effect that the pressing member 24 is kept from shaking.

Meanwhile, the invention is not intended to be limited to the plate spring 25, and a coil spring or another biasing member may also be applied.

Others

In the present exemplary embodiments, sterilization trays that are applied to resin containers 1 as multi-chamber containers have been described; however, the invention is not intended to be limited to this, and the invention can also be applied to single-chamber type resin containers. Furthermore, without being limited to infusion solution containers or drug containers, the sterilization tray can also be used as a sterilization tray for resin containers filled with food products including a liquid or a liquid mixed with a solid, or the like.

Furthermore, it is needless to mention that the invention is not intended to be limited to the exemplary embodiments described above, and various modifications can be made as long as the spirit of the invention is maintained.

EXPLANATION OF REFERENCES

1: resin container
1a: filled part
1b: empty chamber part
1c: partition
1d: stopper part
1e: sterilization trace
10, 10-1, 10-2, 20, 20-1: sterilization tray
12: tray
12a, 22a: support
12b: opening
13, 15: perforated plate
14, 24: pressing member
16, 18: weight
22: tray body
25: plate spring

What is claimed is:

1. A sterilization tray comprising:
   a tray having, on a bottom part thereof, first voids through which at least steam or hot water passes at a time of moist heat sterilization, and configured to place, on the bottom part, a resin container filled with a liquid or a liquid mixed with a solid; and
   a pressing member configured to be placed on the bottom part of the tray so as to hold the resin container between the bottom part of the tray and the pressing member, the pressing member having second voids through which at least steam or hot water passes at the time of moist heat sterilization so as not to prevent sterilization of a part of the resin container, held between the bottom part of the tray and the pressing member, the pressing member pressing at least the peripheral edge of the resin container placed on the tray, between the pressing member and the tray, and preventing deformation of the resin container at the time of moist heat sterilization.

2. The sterilization tray according to claim 1, wherein the tray is constructed from a perforated plate, wire gauze, or a porous member.

3. The sterilization tray according to claim 1, wherein the pressing member is constructed from a porous member, or from a porous member and a weight.

4. The sterilization tray according to claim 1, wherein the pressing member presses at least a region that is not filled with a liquid in the resin container.

5. The sterilization tray according to claim 1, wherein the resin container has a filled part filled with a liquid or a liquid mixed with a solid; and an empty chamber part, and a region in which the resin container is pressed by the pressing member is an entire region of the empty chamber part or a peripheral edge of the empty chamber part.

6. The sterilization tray according to claim 1, wherein the tray is formed into a shape with which the tray can be stacked in a state of accommodating the resin container, and the pressing member is attached in a direction perpendicular to the tray in a freely movable manner and presses the resin container accommodated in second tray immediately therebelow at the time of stacking of the tray and the second tray.

7. The sterilization tray according to claim 6, wherein the pressing member has a spring between the pressing member and the tray, and a biasing force exerted by the spring is applied as a pressing force.

8. A sterilization tray comprising:
   a tray having first voids through which at least steam or hot water passes at a time of moist heat sterilization, and having placed thereon a resin container filled with a liquid or a liquid mixed with a solid; and
   a pressing member having second voids through which at least steam or hot water passes at the time of moist heat sterilization, the pressing member pressing at least the peripheral edge of the resin container placed on the tray, between the pressing member and the tray, and preventing deformation of the resin container at the time of moist heat sterilization,
   wherein the resin container has a filled part and an empty chamber part and wherein the tray has a level difference between a bottom face on which the filled part of the resin container is placed and a bottom face on which the empty chamber part is placed, and the bottom face on which the empty chamber part is placed is formed to be higher by a height equivalent to one-half the height of the filled part than the bottom face on which the filled part of the resin container is placed.

9. The sterilization tray according to claim 6, wherein the tray has an accommodation part accommodating plural resin containers side by side, and plural pressing members are attached to the tray correspondingly to the plural resin containers accommodated in the tray and are independently attached to the tray in a freely movable manner.

10. The sterilization tray according to claim 1, wherein
   in the tray, the bottom on which the resin container is placed is formed from a perforated plate; and
   in openings formed in the perforated plate, when a diameter, in a case in which the openings are round holes, or the minimum width, in a case in which the openings are long holes, is designated as a representative opening length, the representative opening length is from 0.3 mm to 3.3 mm, and
   an opening ratio of the perforated plate is from 2.5% to 15%.

11. The sterilization tray according to claim 10, wherein the representative opening length is from 0.3 mm to 3 mm, and the opening ratio of the perforated plate is from 2.5% to 10%.

12. The sterilization tray according to claim 10, wherein the representative opening length is from 0.8 mm to 1.5 mm, and the opening ratio of the perforated plate is from 4% to 8%.

13. A moist heat sterilization method for sterilizing a resin container filled with a liquid or a liquid mixed with a solid by means of steam or hot water, the method comprising:
   preparing a tray having first voids through which at least steam or hot water passes and a pressing member having second voids through which at least steam or hot water passes;
   placing the resin container on a bottom part of the tray;
   placing the pressing member on the bottom part of the tray so as to hold the resin container between the bottom part of the tray and the pressing member to press at least the peripheral edge of the resin container between the pressing member and the tray as a pre sin process; and
   sterilizing the resin container in a state of being pressed by means of steam or hot water,
   wherein the sterilizing includes sterilizing a part of the resin container, held between the bottom part of the tray and the pressing member, with steam or hot water passing through second voids provided in the pressing member.

14. The moist heat sterilization method according to claim 13, wherein the pressing process is carried out by pressing by means of the pressing member's own weight.

15. The moist heat sterilization method according to claim 13, wherein the pressing process is carried out by pressing by means of the pressing member's own weight and a weight placed on top of the pressing member.

16. The moist heat sterilization method according to claim 13, wherein the pressing process is carried out by pressing by means of the pressing member's own weight and a spring that urges the pressing member from a top side.

* * * * *